June 12, 1962 D. H. MOREY, JR Plant Pat. 2,154
ROSE PLANT
Filed Aug. 1, 1961
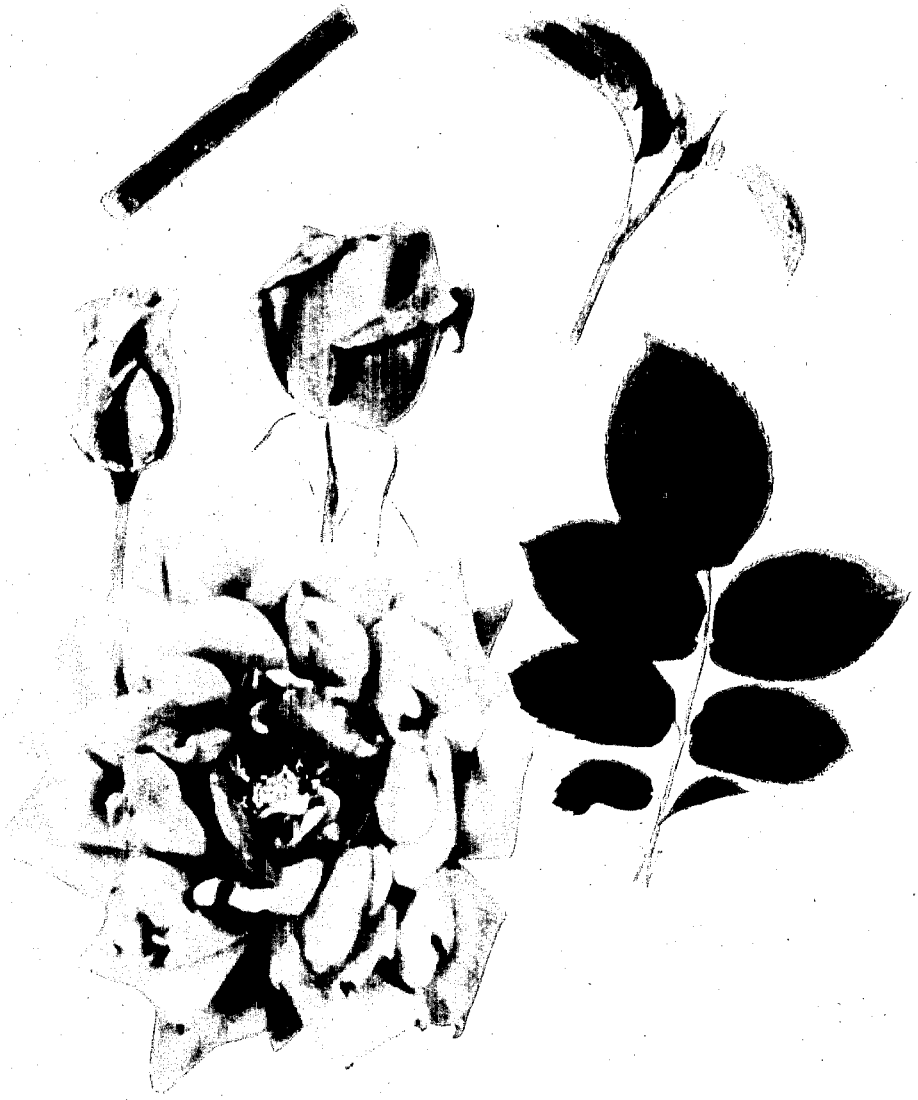
Inventor.
Dennison H. Morey, Jr.
By: Robb & Robb
Attorneys.

United States Patent Office

Plant Pat. 2,154
Patented June 12, 1962

2,154
ROSE PLANT

Dennison H. Morey, Jr., Pleasanton, Calif., assignor to Jackson & Perkins Company, Newark, N.Y., a corporation of New York Filed Aug. 1, 1961, Ser. No. 128,604
1 Claim. (Cl. 47—61)

The present invention relates to a new and distinct variety of rose plant of the hybrid tea class, which was originated by me by crossing the variety "Nocturne" (Plant Patent No. 713) with the variety "Chrysler Imperial" (Plant Patent No. 1,167).

The primary objective of this breeding was to produce a new rose variety having good hardiness and which bears fragrant red flowers suitable for outdoor growing. This objective was achieved, along with other desirable improvements, as evidenced by the following unique combination of characteristics which are outstanding in the new variety and which distinguish it from its parents, as well as from all other varieties of which I am aware:

(1) A vigorous habit of growth and abundant foliage; (2) Good hardiness; (3) A free blooming habit; (4) A very strong flower fragrance; and (5) A distinctive and attractive general color tonality of the flowers corresponding to Carmine, lightly overcast with Spectrum Red, the outer petals of the flowers being deeper in color than the inner or center petals, and corresponding in color to Spectrum Red, overcast with Carmine.

Asexual reproduction of my new variety by budding, as performed at Pleasanton, California, and also at Newark, New York, shows that the foregoing characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with Ridgway's Color Standards and Nomenclature:

Parentage: Seedling.
*Seed parent.*—"Nocturne."
*Pollen parent.*—"Chrysler Imperial."
Classification:
*Botanic.*—Hybrid tea.
*Commercial.*—Hybrid tea.

*Flower*

(Observations made from specimens grown outdoors at Newark, New York, during mid-afternoon in the latter part of the month of September.)

Blooming habit: Recurrent—continuous.
Bud:
*Size.*—Large.
*Form.*—Ovoid; is not affected by wet or hot weather.
*Color.* — When sepals first divide — Oxblood Red, Plate 1. When petals begin to unfurl—Oxblood Red, Plate 1, overcast with Bordeaux, Plate 12, When half-blown: inside of petals — Carmine. Plate 1, lightly overcast with Oxblood Red, Plate 1; reverse of petals—Oxblood Red, Plate 1, overcast with Bordeaux, Plate 12.
*Sepals.*—Slightly branched; curl back when petals begin to unfurl. Color: inside—Chrysolite Green, Plate 31; outside—Cress Green, Plate 31.
*Calyx.*—Color—Biscay Green, Plate 17. Shape—funnel. Size — small. Aspect — smooth. Odor when rubbed—none.
*Peduncle.* — Length — medium. Aspect — smooth. Strength—erect; heavy. Color—Light Yellowish Olive, Plate 30.
*Opening.*—Opens up well; is not affected by adverse weather conditions.

Bloom:
*Size.*—Large. Average size when fully expanded—from 4½ inches to 5½ inches.
*Borne.*—Both singly and several together.
*Stems.*—Long; normal strength.
*Form (when first open).*—Full and high-centered. Permanence—retains its form to the end.
*Petalage.*—Double (full but open center). Number of petals under normal conditions—from 20 to 25.
*Color.*—Center of flower—Oxblood Red, Plate 1, lightly overcast with Carmine, Plate 1. Outer petals—Spectrum Red, Plate 1, overcast with Carmine, Plate 1. Base of petals (aiglet)—Lemon Chrome, Plate 4. Inside of petals — Carmine, Plate 1, lightly overcast with Spectrum Red, Plate 1. Reverse of petals—Carmine, Plate 1, lightly overcast with Scarlet Red, Plate 1. General tonality from a distance — Carmine, Plate 1, lightly overcast with Spectrum Red, Plate 1.
*Discoloration.*—General tonality at end of first day—Oxblood Red, Plate 1, lightly overcast with Carmine, Plate 1. Second day — Carmine, Plate 1, lightly overcast with Spectrum Red, Plate 1. Third day—Carmine, Plate 1, overcast with Spectrum Red, Plate 1.
Petals:
*Texture.* — Thick; is not affected by wet or hot weather.
*Appearance.*—Inside—satiny. Outside—shiny.
*Form.*—Oval.
*Arrangement.*—Imbricated (regularly arranged shingle-like).
*Petaloids in center.*—Few; large.
*Persistence.*—Drop off cleanly.
*Fragrance.*—Strong. Nature—"Old Rose perfume" (centifolia).
*Lasting quality.*—On plant—long. As cut flower—long.

*Genital Organs*

Stamens, anthers: Medium size; many; regularly aranged around styles. Color—Zinc Orange, Plate 15.
Stamens, filaments (threads): Medium length. Color—Spinel Red, Plate 26.
Pollen: Color—Light Buff, Plate 15.
Styles: Columnar; uneven length; medium length; thin.
Stigmas: Color—Warm Buff, Plate 15.
Ovaries: All enclosed in calyx.
Hips: None.
Seeds: None.

*Plant*

Form: Bush.
Growth: Vigorous; upright.
Foliage: Compound of 5–7 leaflets.
*Size.*—Medium.
*Quantity.*—Abundant.
*Color.*—New foliage: upper side—Oil Green, Plate 5, lightly overcast with Victoria Lake, Plate 1; under side—Madder Brown, Plate 13. Old foliage: upper side — Cress Green, Plate 31; under side—Light Cress Green, Plate 31.
*Shape.*—Oval pointed.
*Texture.* — Upper side — leathery. Under side — smooth.
*Ribs and veins.*—Ordinary.
*Edge.*—Serrated (saw-toothed).
*Serration.*—Both double and single; small.

*Leaf stem.*—Color—Walnut Brown, Plate 28. Under side—smooth.

*Stipules.*—Short; smooth.

Wood:

*New wood.*—Color—Oxblood Red, Plate 1. Bark—smooth.

*Old wood.*—Color—Cress Green, Plate 31. Bark—smooth.

Thorns:

*Thorns.*—Quantity: on main stalks from base—ordinary; on laterals from stalk—ordinary. Form—narrow base; medium length; straight. Color (when young)—Oxblood Red, Plate 1. Position—irregular.

*Prickles.*—Quantity: on main stalks—none; on laterals—none.

*Short needles.*—Quantity: on main stalks—none; on laterals—none.

I claim:

A new and distinct variety of rose plant of the hybrid tea class, substantially as herein shown and described, characterized particularly as to novelty by the unique combination of a vigorous habit of growth, abundant foliage, good hardiness, a free blooming habit, a very strong flower fragrance, and a distinctive and attractive general color tonality of the flowers corresponding to Carmine, lightly overcast with Spectrum Red, with the outer flower petals being deeper in color than the inner or center petals and corresponding in color to Spectrum Red, overcast with Carmine.

No references cited.